(12) United States Patent
Fuhr et al.

(10) Patent No.: US 6,572,903 B1
(45) Date of Patent: Jun. 3, 2003

(54) WILDLIFE NUTRITIONAL SUPPLEMENT

(75) Inventors: David R. Fuhr, Winigan, MO (US); David Hauser, Winigan, MO (US)

(73) Assignee: 4 Seasons Wildlife Nutrition, LLC, Winigan, MO (US)

( * ) Notice: Subject to any disclaimer, the term of this patent is extended or adjusted under 35 U.S.C. 154(b) by 0 days.

(21) Appl. No.: 10/063,681

(22) Filed: May 8, 2002

(51) Int. Cl.⁷ .......................... A23L 1/30; A61K 31/65; A61K 31/415
(52) U.S. Cl. ...................... 426/73; 426/72; 426/74; 426/807; 514/152; 514/394; 514/395
(58) Field of Search .......................... 426/73, 72, 74, 426/807; 514/152, 394, 395

(56) References Cited

U.S. PATENT DOCUMENTS

| | | |
|---|---|---|
| 3,246,336 A | 4/1966 | Baribo et al. |
| 4,171,385 A | 10/1979 | Skoch et al. |
| RE31,763 E | 12/1984 | Skoch et al. |
| 4,704,287 A | 11/1987 | Meyer |
| 4,729,896 A | 3/1988 | Sawhill |
| 5,264,227 A | 11/1993 | Laroche et al. |
| 6,261,609 B1 | 7/2001 | Cates, II |
| 6,299,913 B1 | 10/2001 | Block et al. |

OTHER PUBLICATIONS

Schultz, et al, Efficacy of fenbendazole against gastrointestinal nematodes in white–tailed deer. Journal of Range Management. 46:240–244, May 1993.

Howard, Brad and Brian Murphy. Mineral Supplementation-Necessity or Never Mind? Quality Deer Management Association. http://www.qdma.com/articles/detail.asp?ID_97 (undated).

Antler King Deer & Elk Pellet advertisement. http://www.bossbuck.com/products/feed/adpellets.html.

Trophy Image Deer Pellet advertisement. http://www.bossbuck.com/products/feed/tipellets.html.

Sinclair, Stephen, Keith Woodford, Gordon Dryden. Nutrition of Farmed Red and Rusa Deer–Feeding requirements and feed budgeting considerations. Queensland Government, Department of Primary Industries File No. II 0026 (Sep. 1999).

*Primary Examiner*—Kevin E. Weddington
(74) *Attorney, Agent, or Firm*—Anton J. Hopen; Smith & Hopen, P.A.

(57) ABSTRACT

The present invention is a wildlife nutritional supplement for free ranging ruminants including about 7.5–8.5% calcium, about 3.5% phosphorus, about 32–37% salt, at least one "B" series vitamin is selected from a group consisting of pantothenic acid, folic acid, riboflavin, niacin, thiamine, cobalamin, and pyridoxine hydrocholoride, about 16–19% sodium, about 0.15% magnesium, about 0.15% potassium, about 2.5% sulfur, about 1,200 PPM iron, about 20 PPM copper, about 105 PPM manganese, about 45 PPM zinc, about 5 PPM cobalt, about 1 PPM selenium, about 1 PPM iodine, about 50,000 IU/LB Vitamin A, about 20,000 IU/LB Vitamin D, about 50 IU/LB Vitamin E, about 134 MG/LB biotin, about 60 MG/LB ascorbic acid, oxytetracycline and fenbendazole.

15 Claims, No Drawings

WILDLIFE NUTRITIONAL SUPPLEMENT

BACKGROUND OF INVENTION

FIELD OF INVENTION

This invention relates to wildlife nutritional supplements, and more particularly to a ruminant feed supplement having enhanced palatability and immune-system bolstering effects.

The reduction of habitat due to human development has left a noticeable impact on the health and vitality of wild ruminant animals. Ruminant animals such as deer, elk and the like, suffer diminished reproduction, decreased weight, smaller antlers, and susceptibility to disease and parasites.

There are seven major minerals that have an important effect on wildlife: (1) calcium aids in the growth of bones, teeth and antlers and is important in the function of muscles and nerves; (2) phosphorus aids in the growth of bones, teeth and antlers, enhances energy metabolism and enzymation as well as proper protein utilization; (3) potassium is integral in the function of nerves, enzyme processes, as well as mineral and water balance; (4) sulfur is an essential component of some proteins; (5) sodium is vital to the function of muscles and nerves and also maintains water balance; (6) chloride of sodium forms hydrochloric acid in the abomasums which aids in protein breakdown; and (7) magnesium is an important component is almost all body processes.

There are seven trace minerals that are needed to maintain healthy wildlife: (1) manganese is essential for good bone development and feed utilization; (2) copper is needed for blood and feed utilization; (3) zinc provides an important influence on the rate of nutrient absorption; (4) iodine is a vital component of the thyroid hormone which controls body temperature and rate of metabolism; (5) selenium is needed for growth and reproduction and is also involved in enzymatic systems; (6) cobalt is a necessary component of vitamin B12 and enzymes that digest feed; and (7) iron is a critical component of red blood cells.

There are three vitamins known in the prior art for use with wildlife range feed supplements: (1) vitamin A is necessary to support growth, vision, reproduction, is involved in bone development and antler growth, and aids in controlling infections; (2) vitamin D is necessary for the mineralization of bone development and antler growth and maintains proper functioning of muscles, nerves, blood clotting and cellular growth; and (3) vitamin E is a component of the enzyme system, acting as an antioxidant at the cellular level as well as functioning in selenium metabolism.

Supplementing the nutritional deficiencies in range rudiment animals is known in the art. Wildlife nutritional supplements are typically placed near wildlife trails or other areas frequented by wildlife. Commercially available brands include WHITETAIL INSTITUTE 30-06 manufactured by Whitetail Institute Of North America, 239 Whitetail Trail, Pintlala, Ala. 36043, BIOLOGIC manufactured by Haas Outdoors, 200 East Main Street, West Point, Miss. 39773, ANTLER KING manufactured by Antler King Trophy Products, Inc. W11353 Spaulding Road, Black River Falls, Wis. 54615, DEER CANE POWDER and DEER CANE BLOCK manufactured by Evolved Habitats, 2261 Morganza Highway New Roads, La. 70760, BIG SPRINGS TROPHY MINERAL manufactured by BIG SPRINGS TROPHY MINERAL at Rural Route Box 65, Rockport, Ill., 32370, CEDER CREEK TROPHY DEER manufactured by Roger Haslag, P. O. Box 114, Loose Creek, Miss. 65054, and PURINA ELK MINERAL 56/M2 manufactured by Purina Mills, LLC, 1401 South Hanley Road, St. Louis, Miss. 63144. U.S. Pat. No. 6,261,609 describes three iterations of range mineral under the brands of HILL COUNTRY MIX, ROLLING PLAIN MIX and WHEAT PASTURE MINERAL. The components of the above-mentioned supplements are provided in Tables 1–10 below:

TABLE 1

Whitetail Institute 30-06 [t4]

| | | |
|---|---|---|
| Calcium | min | 15% |
| Phosphorus | min | 4% |
| Salt | min | 42% |
| Sodium | | 0 |
| Magnesium | min | 0.82% |
| Potassium | min | 0.22% |
| Sulfur | | 0 |
| Iron | | 0 |
| Copper | ppm | 140 |
| Manganese | ppm | 250 |
| Zinc | ppm | 1400 |
| Cobalt | ppm | 5 |
| Selenium | ppm | 9 |
| Iodine | ppm | 6.7 |
| Vitamin A | iu/lb | 160,000 |
| Vitamin D3 | iu/lb | 50,000 |
| Vitamin E | iu/lb | 50 |
| Folic Acid (B) | | 0 |
| Niacinamide (B3) | | 0 |
| Biotin (H) | | 0 |
| Vitamin C | | 0 |
| Vitamin B1 | | 0 |
| Vitamin B2 | | 0 |
| Vitamin B5 | | 0 |
| Vitamin B6 | | 0 |
| Vitamin B12 | | 0 |
| Does the product clump or set up? | | Yes |
| Medicated mineral option | | No |
| All Natural | | No |
| Year around activity? | | No |
| Insect control? Ticks and gnats | | No |

TABLE 2

Bio Logic [t1]

| | | |
|---|---|---|
| Calcium | min | 19.6% |
| Phosphorus | min | 9.8% |
| Salt | min | 67% |
| Sodium | | 0 |
| Magnesium | | 0 |
| Potassium | min | 0.65% |
| Sulfur | | 0 |
| Iron | | 0 |
| Copper | | 0 |
| Manganese | | 0 |
| Zinc | | 0 |
| Cobalt | | 0 |
| Selenium | | 0 |
| Iodine | | 0 |
| Vitamin A | iu/lb | 520,000 |
| Vitamin D3 | iu/lb | 110,000 |
| Vitamin E | | 0 |
| Folic Acid | | 0 |
| Niacinamide (B3) | | 0 |
| Biotin (H) | | 0 |
| Vitamin C | | 0 |
| Vitamin B1 | | 0 |
| Vitamin B2 | | 0 |
| Vitamin B5 | | 0 |
| Vitamin B6 | | 0 |
| Vitamin B12 | | 0 |
| Does the product clump or set up? | | Yes |
| Medicated mineral option | | No |
| All natural | | No |

TABLE 2-continued

Bio Logic
[t1]

| | | |
|---|---|---|
| Year around activity? | | No |
| Insect control? Ticks and gnats | | No |

TABLE 3

Antler King
[t3]

| | | |
|---|---|---|
| Calcium | min | 17% |
| Phosphorus | min | 8.5% |
| Salt | min | 21% |
| Sodium | | 0 |
| Magnesium | min | 1.2% |
| Potassium | min | 0.9% |
| Sulfur | | 0 |
| Iron | ppm | 50 |
| Copper | ppm | 40 |
| Manganese | ppm | 120 |
| Zinc | ppm | 200 |
| Cobalt | ppm | 4.5 |
| Selenium | ppm | 20 |
| Iodine | ppm | 0.6 |
| Vitamin A | iu/lb | 11,000 |
| Vitamin D3 | iu/lb | 1,000 |
| Vitamin E | iu/lb | 10 |
| Folic Acid (B) | | 0 |
| Niacinamide (B3) | | 0 |
| Biotin (H) | | 0 |
| Vitamin C | | 0 |
| Vitamin B1 | | 0 |
| Vitamin B2 | | 0 |
| Vitamin B5 | | 0 |
| Vitamin B6 | | 0 |
| Vitamin B12 | | 0 |
| Does the product clump or set up? | | Yes |
| Medicated mineral option | | No |
| All natural | | No |
| Year around activity? | | No |
| Insect control? Ticks and gnats | | No |

TABLE 4

Deer Cane Powder
[t2]

| | | |
|---|---|---|
| Calcium | | 0 |
| Phosphorus | | 0 |
| Salt | min | 50% |
| Sodium | min | 40% |
| Magnesium | | 0 |
| Potassium | | 0 |
| Sulfur | | 0 |
| Iron | | 0 |
| Copper | | 0 |
| Manganese | | 0 |
| Zinc | | 0 |
| Cobalt | | |
| Selenium | | 0 |
| Iodine | | 0 |
| Vitamin A | | 0 |
| Vitamin D3 | | 0 |
| Vitamin E | | 0 |
| Folic Acid (B) | | 0 |
| Niacinamide (B3) | | 0 |
| Biotin (H) | | 0 |
| Vitamin C | | 0 |
| Vitamin B1 | | 0 |
| Vitamin B2 | | 0 |
| Vitamin B5 | | 0 |
| Vitamin B6 | | 0 |
| Vitamin B12 | | 0 |

TABLE 4-continued

Deer Cane Powder
[t2]

| | |
|---|---|
| Does product clump or set up? | No |
| Medicated mineral option | No |
| All Natural | No |
| Year around activity? | Yes |
| Insect control? Ticks and gnats | No |

TABLE 5

Big Springs Trophy Mineral
[t5]

| | | |
|---|---|---|
| Calcium | min | 15.5% |
| Phosphorus | min | 8.5% |
| Salt | min | 21.5% |
| Sodium | | 0 |
| Magnesium | min | 1.2% |
| Potassium | min | 1.4% |
| Sulfur | min | 2.3% |
| Iron | ppm | 4400 |
| Copper | | 0 |
| Manganese | ppm | 1900 |
| Zinc | ppm | 2750 |
| Cobalt | ppm | 22 |
| Selenium | ppm | 1.5 |
| Iodine | ppm | 45 |
| Vitamin A | iu/lb | 50,000 |
| Vitamin D3 | iu/lb | 5,000 |
| Vitamin E | iu/lb | 20 |
| Folic Acid (B) | | 0 |
| Niacinamide (B3) | | 0 |
| Biotin (H) | | 0 |
| Vitamin C | | 0 |
| Vitamin B1 | | 0 |
| Vitamin B2 | | 0 |
| Vitamin B5 | | 0 |
| Vitamin B6 | | 0 |
| Vitamin B12 | | 0 |
| Does product clump or set up? | | Unknown |
| Medicated mineral option | | No |
| All natural | | No |
| Year around activity? | | No |
| Insect control? Ticks and gnats | | No |

TABLE 6

Cedar Creek Trophy Deer
[t6]

| | | |
|---|---|---|
| Calcium | min | 15.5% |
| Phosphorus | min | 8.5% |
| Salt | min | 21.5% |
| Sodium | | 0 |
| Magnesium | min | 1.2% |
| Potassium | min | 1.4% |
| Sulfur | min | 2.3% |
| Iron | ppm | 4400 |
| Copper | | 0 |
| Manganese | ppm | 1900 |
| Zinc | ppm | 2750 |
| Cobalt | ppm | 22 |
| Selenium | ppm | 1.5 |
| Iodine | ppm | 45 |
| Vitamin A | iu/lb | 50,000 |
| Vitamin D3 | iu/lb | 5,000 |
| Vitamin E | iu/lb | 20 |
| Folic Acid (B) | | 0 |
| Niacinamide (B3) | | 0 |
| Biotin (H) | | 0 |
| Vitamin C | | 0 |
| Vitamin B1 | | 0 |
| Vitamin B2 | | 0 |

TABLE 6-continued

Cedar Creek Trophy Deer
[t6]

| | | |
|---|---|---|
| Vitamin B5 | | 0 |
| Vitamin B6 | | 0 |
| Vitamin B12 | | 0 |
| Does product clump or setup? | | Unknown |
| Medicated mineral option | | No |
| All natural | | No |
| Year around activity? | | No |
| Insect control? Ticks and gnats | | No |

TABLE 7

Hill Country Mix
[t7]

| | | |
|---|---|---|
| Calcium | min | 0% |
| Phosphorus | min | 7.80% |
| Salt | min | 22.50% |
| Sodium | | 0 |
| Magnesium | min | 2.00% |
| Potassium | min | 4.00% |
| Sulfur | min | 9.94% |
| Iron | min | 0.01% |
| Copper | min | 0.005% |
| Manganese | min | 0.10% |
| Zinc | min | 0.04% |
| Cobalt | min | 0.002% |
| Selenium | min | 0.0025% |
| Iodine | min | 0.006% |
| Vitamin A | iu/lb | 200,000 |
| Vitamin D3 | iu/lb | 40,000 |
| Vitamin E | iu/lb | 200 |
| Folic Acid (B) | | 0 |
| Niacinamide (B3) | | 0 |
| Biotin (H) | | 0 |
| Vitamin C | | 0 |
| Vitamin B1 | | 0 |
| Vitamin B2 | | 0 |
| Vitamin B4 | | 0 |
| Vitamin B6 | | 0 |
| Vitamin B12 | | 0 |
| Does product clump or setup? | | Unknown |
| Medicated mineral option | | Unknown |
| All natural | | Unknown |
| Year around activity? | | No |
| Insect control? Ticks and gnats | | No |

TABLE 8

Rolling Plain Mix
[t8]

| | | |
|---|---|---|
| Calcium | min | 0% |
| Phosphorus | min | 5.20% |
| Salt | min | 27.50% |
| Sodium | | 0 |
| Magnesium | min | 2.23% |
| Potassium | min | 5.38% |
| Sulfur | min | 10.48% |
| Iron | min | 0.01% |
| Copper | min | 0.005% |
| Manganese | min | 0.10% |
| Zinc | min | 0.04% |
| Cobalt | min | 0.002% |
| Selenium | min | 0.025% |
| Iodine | min | 0.006% |
| Vitamin A | iu/lb | 200,000 |
| Vitamin D3 | iu/lb | 40,000 |
| Vitamin E | iu/lb | 200 |
| Folic Acid (B) | | 0 |
| Niacinamide (B3) | | 0 |
| Biotin (H) | | 0 |

TABLE 8-continued

Rolling Plain Mix
[t8]

| | | |
|---|---|---|
| Vitamin C | | 0 |
| Vitamin B1 | | 0 |
| Vitamin B2 | | 0 |
| Vitamin B5 | | 0 |
| Vitamin B6 | | 0 |
| Vitamin B12 | | 0 |
| Does product clump or setup? | | Unknown |
| Medicated mineral option | | Unknown |
| All natural | | Unknown |
| Year around activity? | | No |
| Insect control? Ticks and gnats | | No |

TABLE 9

Wheat Pasture Mineral
[t9]

| | | |
|---|---|---|
| Calcium | min | 5.00% |
| Phosphorus | min | 6.30% |
| Salt | min | 20.80% |
| Sodium | | 0 |
| Magnesium | min | 7.56% |
| Potassium | min | 0% |
| Sulfur | min | 8.67% |
| Iron | min | 0.01% |
| Copper | min | 0.09% |
| Manganese | min | 0.20% |
| Zinc | min | 0.25% |
| Cobalt | min | 0.001% |
| Selenium | min | 0.002% |
| Iodine | | 0 |
| Vitamin A | iu/lb | 10,000 |
| Vitamin D3 | iu/lb | 25,000 |
| Vitamin E | iu/lb | 400 |
| Folic Acid (B) | | 0 |
| Niacinamide (B3) | | 0 |
| Biotin (H) | | 0 |
| Vitamin C | | 0 |
| Vitamin B1 | | 0 |
| Vitamin B2 | | 0 |
| Vitamin B5 | | 0 |
| Vitamin B6 | | 0 |
| Vitamin B12 | | 0 |
| Does the product clump or setup? | | Unknown |
| Medicated animal option | | Unknown |
| Medicated mineral option | | Unknown |
| All natural | | Unknown |
| Year around activity? | | No |
| Insect control? Ticks and gnats | | No |

TABLE 10

Purina Elk Mineral 56/M2
[t10]

| | | |
|---|---|---|
| Calcium | min | 10.50% |
| Phosphorus | min | 10.00% |
| Salt | min | 19.50% |
| Sodium | | 0 |
| Magnesium | min | 5.00% |
| Potassium | | 0 |
| Sulfur | | 0 |
| Iron | | 0 |
| Copper | | 0 |
| Manganese | | 0 |
| Zinc | | 0 |
| Cobalt | | 0 |
| Selenium | ppm | 60 |
| Iodine | | 0 |
| Vitamin A | iu/lb | 250,000 |
| Vitamin D3 | iu/lb | 60,000 |

TABLE 10-continued

Purina Elk Mineral 56/M2
[t10]

| | | |
|---|---|---|
| Vitamin E | iu/lb | 550 |
| Folic Acid (B) | | 0 |
| Niacinamide (B3) | | 0 |
| Biotin (H) | | 0 |
| Vitamin C | | 0 |
| Vitamin B1 | | 0 |
| Vitamin B2 | | 0 |
| Vitamin B5 | | 0 |
| Vitamin B6 | | 0 |
| Vitamin B12 | | 0 |
| Does product clump or setup? | | Yes |
| Medicated mineral option | | Unknown |
| All natural | | Unknown |
| Year around activity | | Unknown |
| Insect control? Ticks and gnats | | No |

Although the above-mentioned products enhance the health of the wildlife, drawbacks to current formulations still remain. Nutritional deficiencies that contribute to decrease repellency of ticks, mosquitoes, gnats and flies are still not addressed by the known art.

Another need in the art exists for sustained palatability and consumption. The effectiveness of the prior art supplements is restrained by the inconsistent and limited consumption of the product. Wildlife suffering from mineral and vitamin deficiencies benefit from ongoing and consistent intake of supplements, rather than sporadic consumption.

Another need in the art exists for a wildlife supplement that preemptively medicates ruminant animals against parasitic and bacteria infections while maintaining the beneficial flora needed for proper digestion.

Yet another need in the art exists for a wildlife supplement that includes the addition of "B" and "C" series vitamins that maintain the overall health of ruminant animals. Currently, "B" and "C" series vitamins are only provided in a penned or controlled environment and administered through veterinary means.

It is, therefore, to the effective resolution of the aforementioned problems and shortcomings of the prior art that the present invention is directed.

However, in view of the prior art in at the time the present invention was made, it was not obvious to those of ordinary skill in the pertinent art how the identified needs could be fulfilled.

DETAILED DESCRIPTION

The present invention advances the art in taken several counter-intuitive and non-obvious approaches to its nutritional supplement. Studies analyzing the effectiveness of these approaches reveal substantial and unexpected advantages.

As indicated above, calcium and phosphorus are two critical components in nutritional supplements. In the prior art supplements, calcium, when present, is provided at a minimum percentage of 5–19.6% and phosphorus at a minimum percentage of 4%. However, studies conducted in support of the present invention have determined that the larger amounts of calcium and phosphorous, while nutritionally beneficial to the animal, limit the overall intake or consumption. The present invention reduces the amounts to a lower level and added sodium and salt as the main attractant. As a result, an increase in regular consumption, year-round usage and overall greater intake of calcium and phosphorus was achieved. While the prior art teaches an increase in levels of calcium and phosphorus, both vital for health, the novel approach of the present invention diverges from the suggestions of the prior art to obtain a superior overall intake level of these mineral components. Through this increased intake, primarily due to the sodium, more flexibility is available to modify the nutritional formulations to address additional health issues.

The prior art teaches that "B" series vitamins are not required, and thus should not be a part of a range fed ruminant supplement. As indicated above by the published breakdown of components in the prior art supplements, "B" series vitamins and their associated sources are absent from the formulations. In addition to the perceived unimportance of the "B" series need, the inclusion of "B" series vitamins would offset formulas known in the prior art. Due to the present invention's novel formulation of calcium and phosphorus, flexibility exists in the present invention to examine the effectiveness of this heretofore disregarded vitamin in this application.

"B" series vitamins can be broken down into eight main groups: (1) vitamin B-1 (thiamin) is a catalyst in carbohydrate metabolism enabling carbohydrates to release energy while also serving as a natural insect repellent; (2) vitamin B-2 (riboflavin) acts as a critical cofactor or coenzyme in the metabolism of fats, carbohydrates and amino acids, deficiency causes skin an corneal lesions; (3) vitamin B-3 is critical to cellular respiration and essential for the metabolism of carbohydrates and fats; (4) vitamin B-5 is required in the metabolism of fat, protein and carbohydrates; (5) vitamin B-6 (pyridoxal) is required in the synthesis and metabolism of protein and amino acids while also supporting the formation of red blood cells; (6) vitamin B-12 (cobalamin) is critical to normal nerve cell activity, DNA replication and the development of red blood cells; (7) biotin (also known as vitamin H) services as a critical cofactor in the metabolism of carbohydrates, proteins and fats while also aiding in antler growth; and (8) folic acid (tetrahydrofolate) plays an important role in the synthesis of nucleic acids.

Prior art literature suggests that the inclusion of "B" series vitamins is unneeded as ruminant animals obtain this vitamin through available resources. However, such ideal environmental conditions are not always present, particularly in arid, dry regions. Accordingly, deficiencies in "B" series vitamins lead to increased insect bites, ticks and otherwise diminished immune system strength. Responsive to the available flexibility due to the reduction of calcium and phosphorus levels, "B" series vitamin components are included in this novel formulation with substantial empirical improvements in the well-being of the animals.

Vitamin C or ascorbic acid is important in the hydroxylation of collagen which in its absence is inadequately hydroxylated. The defective collagen produces the skin lesions and blood vessel weaknesses which are characteristic of scurvy, the deficiency disease of this vitamin.

Literature has noted 32 species of gastrointestinal nematodes have been recorded in white-tailed deer, several of which also infect livestock. (Prestwood, A. K., and S. R. Pursglove. 1981. Gastrointestinal nematodes, p. 318–350. In: W. R. Davidson, F. A. Hayes, V. F. Nettles, and F. E. Kellogg (eds.), Diseases and parasites of white-tailed deer. Tall Timbers Res. Sta. Misc. Pub. 7, Tallahassee, Fla.) Fenbendazole provided to captive and free-ranging white-tailed deer reduced gastrointestinal nematode burdens. (Schultz, et. Al, Efficacy of fenbendazole against gastrointestinal nematodes in white-tailed deer. Journal of Range Management. 46:240–244, May 1993). While the 1993 reference suggests the application of fenbendazole to free-rangeruminant animals, the prior art formulas were rigidly formulated and unable to accommodate additional medicinal components. However, the present invention conserves much needed flexibility in its formulation by the novel modification in core minerals that unexpectedly enhance palatability, and thus overall consumption. Therefore, the inclusion of anthelminthic, and more particularly, fenbendazole, is possible under the present formulation.

In addition to the inclusion of a de-wormer, the present formulation provides flexibility to include an antibiotic. Periodic inducement into the animals' diet functions similar to an antibiotic in humans. A particular advantage of employing oxytetracycline is that the animal uses what it needs and discards the rest through its natural waste system. Accordingly, the present novel formulation cannot be over used leading to detrimental effects.

The present invention is a wildlife nutritional supplement for free choice fed ruminants including in granular or block form about 7.5–8.5% calcium, about 3.5% phosphorus, about 32–37% salt, at least one "B" series vitamin is selected from a group consisting of pantothenic acid, folic acid, riboflavin, niacin, thiamine, cobalamin, and pyridoxine hydrochloride, about 16–19% sodium, about 0.15% magnesium, about 0.15% potassium, about 2.5% sulfur, about 1,200 PPM iron, about 20 PPM copper, about 105 PPM manganese, about 45 PPM zinc, about 5 PPM cobalt, about 1 PPM selenium, about 1 PPM iodine, about 50,000 IU/LB Vitamin A, about 20,000 IU/LB Vitamin D, about 50 IU/LB Vitamin E, about 134 MG/LB biotin, about 60 MG/LB ascorbic acid, oxytetracycline and fenbendazole.

In a liquid medium embodiment, the invention includes about 17–18% calcium, about 9% phosphorus, about 11–12% salt, at least one "B" series vitamin selected from a group consisting of pantothenic acid, folic acid, riboflavin, niacin, thiamine, cobalamin, and pyridoxine hydrocholoride, about 10–11% sodium, about 3.7% magnesium, about 3.7% potassium, about 0.0037% sulfur, about 1,666 PPM iron, about 185 PPM copper, about 60 PPM manganese, about 1,388 PPM zinc, about 2 PPM cobalt, about 0.57 PPM selenium, about 13 PPM iodine, about 50,000 IU/LB Vitamin A, about 20,000 IU/LB Vitamin D, about 50 IU/LB Vitamin E, about 134 MG/LB biotin, about 60 MG/LB ascorbic acid, oxytetracycline and fenbendazole.

It is therefore an object of the present invention to provide a more palatable supplement that provides enhanced, long-term intake of vital minerals and vitamins while providing formulaic flexibility to include de-worming and antibiotic components.

It is another object of the present invention to provide a nutritional supplement that enhances the natural immune system of the ruminant animal.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A wildlife nutritional supplement for free choice fed ruminants comprising about 7.5–8.5% calcium and about 3.5% phosphorus.

2. The wildlife nutritional supplement of claim 1 wherein the composition is granulated.

3. The wildlife nutritional supplement of claim 1 wherein the composition is blocked.

4. The wildlife nutritional supplement of claim 1 further comprising about 32–37% salt.

5. The wildlife nutritional supplement of claim 1 further comprising at least one "B" series vitamin.

6. The wildlife nutritional supplement of claim 5 wherein the at least one "B" series vitamin selected from a group consisting of pantothenic acid, folic acid, riboflavin, niacin, thiamine, biotin, cobalamin, and pyridoxine hydrocholoride.

7. The wildlife nutritional supplement of claim 1 further comprising at least one "G" series vitamin.

8. The wildlife nutritional supplement of claim 1 further comprising at least one "H" series vitamin.

9. The wildlife nutritional supplement of claim 1 further comprising ascorbic acid.

10. The wildlife nutritional supplement of claim 6 further comprising about 16–19% sodium, about 0.15% magnesium, about 0.15% potassium, about 2.5% sulfur, about 1,200 PPM iron, about 20 PPM copper, about 105 PPM manganese, about 45 PPM zinc, about 5 PPM cobalt, about 1 PPM selenium, about 1 PPM iodine, about 50,000 IU/LB Vitamin A, about 20,000 IU/LB Vitamin D, about 50 IU/LB Vitamin E, about 134 MG/LB biotin, and about 60 MG/LB ascorbic acid.

11. The wildlife nutritional supplement of claim 1 further comprising an antibiotic.

12. The wildlife nutritional supplement of claim 11 wherein the antibiotic comprises oxytetracycline.

13. The wildlife nutritional supplement of claim 1 further comprising an anthelminthic component.

14. The wildlife nutritional supplement of claim 13 wherein the anthelminthic component comprises fenbendazole.

15. A wildlife nutritional supplement for free ranging ruminants comprising about 7.5–8.5% calcium, about 3.5% phosphorus, about 32–37% salt, at least one "B" series vitamin is selected from a group consisting of pantothenic acid, folic acid, riboflavin, niacin, thiamine, biotin, cobalamin, and pyridoxine hydrocholoride, about 16–19% sodium, about 0.15% magnesium, about 0.15% potassium, about 2.5% sulfur, about 1,200 PPM iron, about 20 PPM copper, about 105 PPM manganese, about 45 PPM zinc, about 5 PPM cobalt, about 1 PPM selenium, about 1 PPM iodine, about 50,000 IU/LB Vitamin A, about 20,000 IU/LB Vitamin D, about 50 IU/LB Vitamin E, about 134 MG/LB biotin, about 60 MG/LB ascorbic acid, oxytetracycline and fenbendazole.

* * * * *